United States Patent [19]
de Souza et al.

[11] Patent Number: 5,869,523
[45] Date of Patent: Feb. 9, 1999

[54] PROCESS FOR THE PREPARATION OF 6-(SUBSTITUTEDAMINOPROPIONYL)-DERIVATIVES OF FORSKOLIN

[75] Inventors: Noel John de Souza; Adolf D'Sa; Samba Laxminarayan Kattige, all of Bombay; Gulab Bajirao Padwal, New Bombay; Jürgen Blumbach, Bombay, all of India

[73] Assignee: Hoechst Aktiengesellschaft, Frankfurt am Main, Germany

[21] Appl. No.: 733,641

[22] Filed: Jul. 22, 1991

[30] Foreign Application Priority Data

Jul. 24, 1990 [EP] European Pat. Off. ............. 90114124

[51] Int. Cl.$^6$ .................... C07D 309/20; A61K 31/35
[52] U.S. Cl. ................... 514/459; 514/460; 549/13; 549/28; 549/417; 549/419; 549/420; 549/423
[58] Field of Search ................. 549/424, 13, 28, 549/417, 419, 420, 423; 514/459, 460

[56] References Cited

FOREIGN PATENT DOCUMENTS 2 205 564  12/1988  United Kingdom .

OTHER PUBLICATIONS

B. Lal et al., "Aluminum Chloride as a Powerful Catalyst for the Preparation of O–Isopropylidene and O–Benzylidene Derivatives of Labdanes", Synthesis, 9:711–713 (1989).

Primary Examiner—Johann Richter
Assistant Examiner—Michael B. Hydorn
Attorney, Agent, or Firm—Finnegan, Henderson, Farabow, Garrett & Dunner

[57] ABSTRACT

Process for the preparation of 6-(substitutedaminopropionyl)-derivatives of forskolin Process for the manufacture of 6β-(3-substitutedamino) propionyloxy forskolin derivatives of the general formula 4 Claims, 2 Drawing Sheets

PROCESS FOR THE PREPARATION OF 6-(SUBSTITUTEDAMINOPROPIONYL)-DERIVATIVES OF FORSKOLIN

DESCRIPTION

Process for the preparation of 6-(substitutedaminopropionyl)-derivatives of forskolin This invention relates to a process for the synthesis of 6-β-(3-substitutedamino)propionyloxyforskolin derivatives, a series of compounds displaying pharmacological properties, especially cardiovascular properties such as positive inotropic, antihypertensive and vasodilatory activity represented by the general formula I,

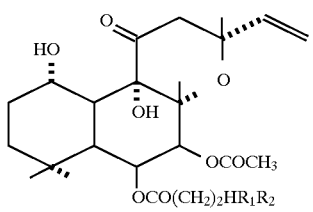

wherein $R_1$ and $R_2$ each stands for hydrogen, alkyl, aryl, aralkyl or dialkylaminoalkyl; or $R_1$ and $R_2$ together with the nitrogen to which they are attached form a heterocycle which may contain an additional heteroatom such as N, O, S and may optionally be substituted at one or more positions by groups such as alkyl, alkoxy, hydroxyl, halogen or aryl and pharmaceutically acceptable salts thereof. Such compounds are of high interest especially because of compound NKH-477, a 6-substitutedaminopropionylforskolin derivative, which is a very useful in the treatment of congestive heart failure.

The term alkyl stands for a $C_1$–$C_6$, preferably $C_1$–$C_4$ straight or branched chain such a methyl, ethyl, propyl, isopropyl, n-butyl, tert butyl or n-pentyl.

The term aryl stands for phenyl, optionally substituted with groups such as $C_1$–$C_4$-alkyl, $C_1$–$C_4$-alkoxy, hydroxyl, halogen such as chlorine or fluorine, nitro, cyano or trifluoromethyl.

The term aralkyl stands for benzyl, wherein phenyl has the same meanings defined above.

The term dialkylaminoalkyl stands for groups such as for example dimethylaminopropyl or diethylaminobutyl.

The term heterocycle stands for groups such as e.g. morpholino, piperidino, pyrrolidino, piperazino or homopiperidino, which may be substituted preferably by $C_1$–$C_4$-alkyl.

Pharmaceutically acceptable salts means salts of inorganic and organic acids such as hydrochloric acid, hydrobromic acid, sulphonic acid, phosphoric acid, formic acid, acetic acid, maleic acid, citric acid, tartaric acid, lactic acid, methane-sulphonic acid.

BACKGROUND OF THE INVENTION

Compounds of the formula I belong to the series of water-soluble aminoacyl forskolin derivatives which display potent pharmacological properties. They are the subject of different patent applications and publications viz. EP application No. 0222413, Synthesis 711, 1989 Indian Pat. Appl. No. 164675, Ger. Pat. appln. No. 3623300-5. J.P. Appln. No. 159638, Ind. Pat. Appln. No. 238/BOM/87, Ger. Pat. Appl. No. 3737353.6, Mol. Pharmacol., 32, 133 (1987). Processes for their preparation have also been described. The different sequence through which compounds of the formula I have been prepared can be summarised as shown in FIG. 1:

Inventive steps of the current invention:

In view of the high importance of compounds of the formula I for use in cardiovascular drug therapy, different inventive steps have been introduced in a process for their preparation using the 1,9-O-isopropylidene protecting group in forskolin.

1st Inventive Step: The 1,9-O-isopropylidene derivative of forskolin has surprisingly been now found to be formed in almost quantitative yield (96–97%) through reaction of forskolin with acetone in the presence of hydrogen chloride, in contrast with the earlier process using anhydrous aluminum chloride/ether/acetone (cf. Syn. Synthesis 711–713, 1989).

2nd Inventive Step: The treatment of the 1,9-O-isopropylidene derivative of 7-deacetylforskolin with β-halopropionylhalide, preferably β-chloropropionylchloride and triethylamine in toluene has surprisingly been now found to result in the formation of the novel 1,9-O-isopropylidene derivative of 7β-acryloyloxyforskolin in >90% yield.

3rd Inventive Step: Treatment of the 1,9-O-isopropylidene derivative of 7β-acryloyloxyforskolin with aqueous sodium hydroxide in acetonitrile has surprisingly been now found to result in the formation of the novel 1,9-O-isopropylidene derivative of 6β-acryloyloxy-7-deacetylforskolin in >90% yields.

More specifically the invention describes a process for the preparation of compounds of the formula I according to the sequence shown in FIG. 2.

Figure 1:
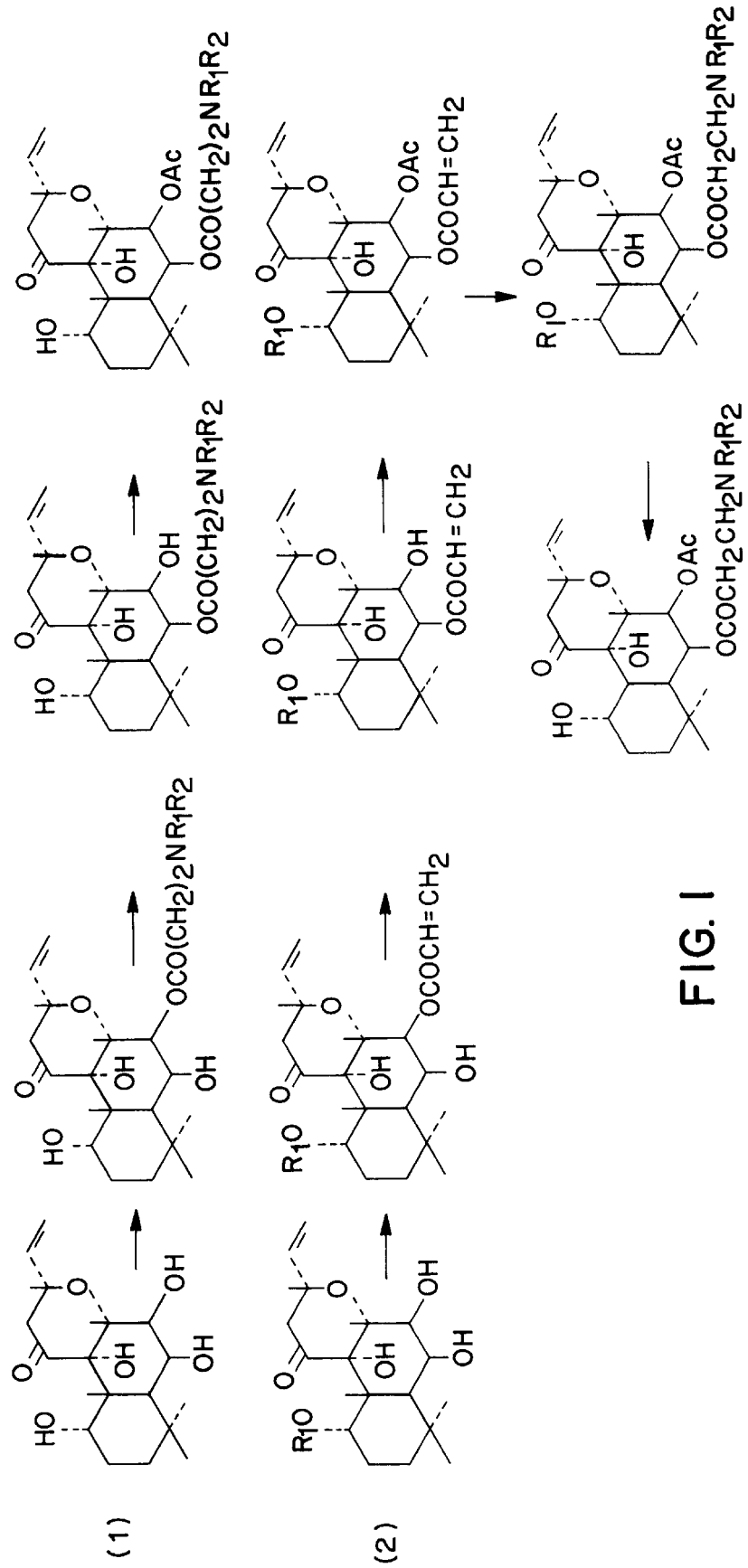
FIG. 1 summarizes different sequences through which the compounds of formula (I) can be prepared.
Figure 2:
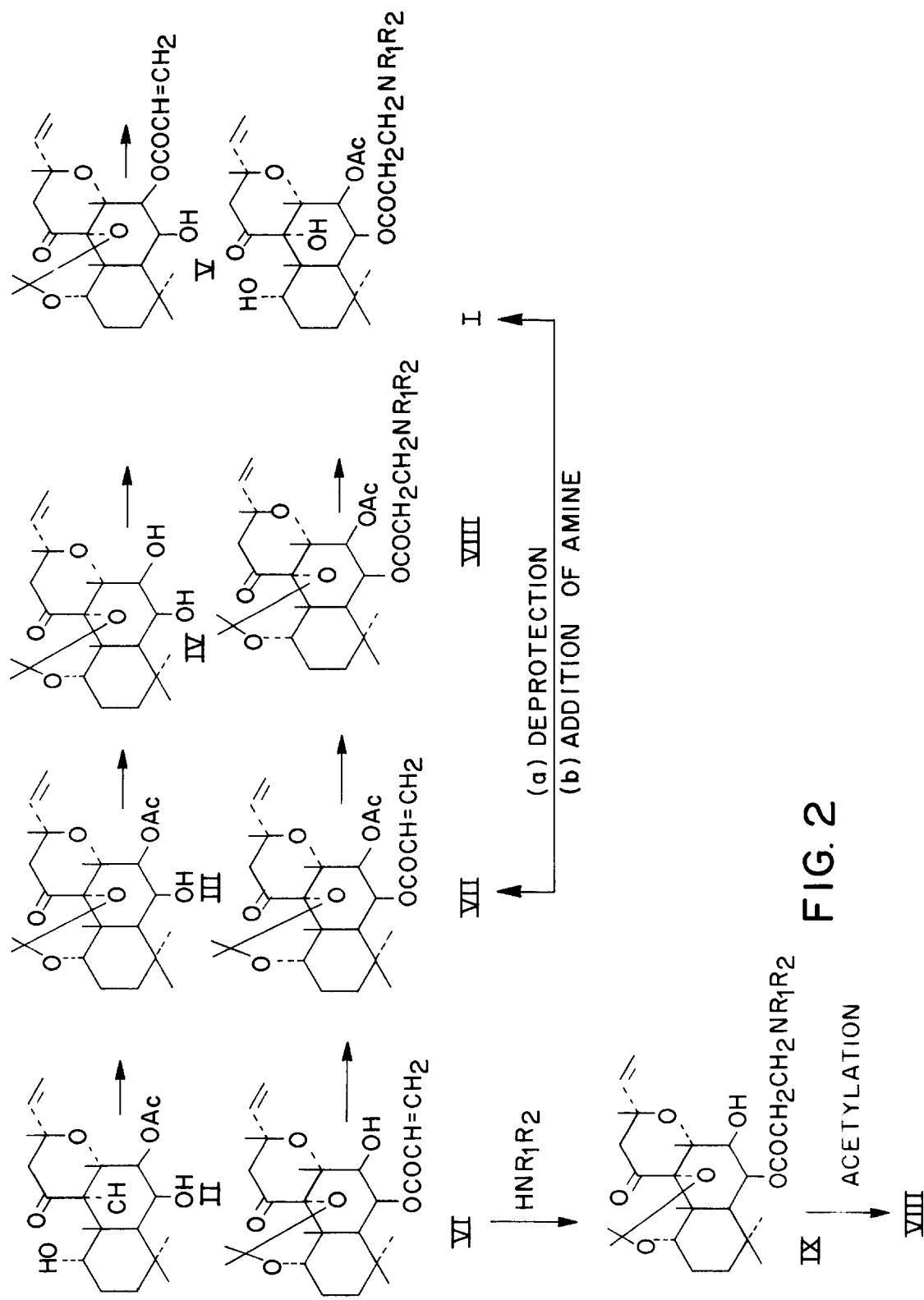
FIG. 2 describes the preparation of the compounds of formula (I) according to the invention.

According to the process of the invention, a solution of forskolin (II) in anhydrous acetone, chilled to about 0°–5° C., was subjected to a stream of hydrogen chloride for about 5–30 mins. to provide the 1,9-O-isopropylidene derivative (III) in >96% yield.

A solution of compound III in an alkanol, for example methanol, was treated with an alkali, for example aqueous sodium hydroxide, at temperatures ranging from ambient to about 60° C. for about 0.2–1.0 hour to provide the 7-deacetyl derivative (IV) in >97% yield.

A solution of compound IV in an organic solvent, for example toluene, was treated with a solution of preferably β-chloropropionyl chloride in the same solvent in the presence of base such as e.g. triethylamine at temperatures ranging from about 0.5° C., rising up to ambient temperatures, for a period of about 1–5 hours, to provide the novel 7β-acryloyl derivative (V) in >90% yield.

A solution of compound V in an organic solvent, for instance acetonitrile, isopropanol, acetone, was treated with alkali, for example aqueous sodium hydroxide, potassium hydroxide, sodium carbonate, potassium carbonate at about 0°–5° C. for about 1–5 hours to provide the novel 6β-acryloyl derivative (VI) in >90%–95% yield.

Compound VI was acetylated in known manner, e.g. in solution in a mixture of acetic anhydride/pyridine which—when left overnight—provided the 7-acetyl derivative (VII) in a yield >93%. Other acylating reagents are acetylchloride or acetylchloride/pyridine optionally in the presence of an organic solvent such as methylene chloride.

The overall yield of compound VII from compound II is ca. 70%.

Compound VII was treated with an appropriate amine to obtain compound VIII. Alternatively compound VIII was obtained by treating the compound VI with an appropriate amine optionally using organic solvents to obtain compound IX and subsequent acetylation e.g. with a mixture of acetic anhydride-pyridine at room temperature. Compound VIII was then deprotected at the 1,9-positions to give the desired compound I by adjusting the pH value of the solution to about 1.0–3.5, preferably 1.0–1.3, at a temperature ranging from about 0° C. to 80° C., preferably 25°–60° C., for a period up to about 72 hours, preferably for less than 1 hour up to 24 hours. Alternatively, there could be done a reversal of the procedure, that is first deprotection at the 1,9-position and then treatment with an appropriate amine by the procedures described above.

Also, a further part of the invention comprises a combination of some of the sequence steps in a one-pot reaction so that an overall shorter synthetic sequence can be operated. For instance, such a shorter sequence may be

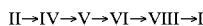

II→IV→V→VI→VIII→I

Working examples 8 and 9 illustrate the conversations of Compound II to Compound IV and of Compound VI to Compound VIII. Working Example 11 describes the part of the invention, wherein Compound VIII may be simultaneously deprotected and converted to its acid addition salt in one step by treatment with the appropriate acid, for instance with hydrochloric acid, using a strength of acid to provide a pH environment of <0.1 to <0.5 at a temperature of below 0° C. to 30° C., for a period up to 5 hours.

The following compounds are preferred compounds of the invention:

1. 7β-Acetoxy-6β-[(3-dimethylaminopropionyl)oxy]-1α, 9α-dihydroxy-8,13-epoxy-labd-14-en-11-one hydrochloride.
2. 7β-Acetoxy-6β-[(3-piperidinopropionyl)oxy]-1α, 9α-dihydroxy-8,13epoxy-labd-14-en-11-one hydrochloride hemihydrate.
3. 7β-Acetoxy-6β-[(3-N-methylpiperazinopropionyl) oxy]-1α,9β0 -dihydroxy-8,13-epoxy-labd-14-en-11-one hydrochloride.
4. 7β-Acetoxy-6β-[(3-morpholinopropionyl)oxy]-1α,9α-dihydroxy-8,13-epoxy-labd-14-en-11-one hydrochloride.

Yield of compound I ($NR_1R_2$=$(CH_3)_2N$) following the procedure of the invention is ca. 62% (based on forskolin as starting material). This yield is higher than any other previous reported yield of the compound.

The following examples describe the invention, without limiting the scope of the invention.

EXAMPLE 1

7β-Acetoxy-6β-hydroxy-1,9-O-isopropylidene-8,13-epoxy-labd-14-en-11-one (III)

Forskolin (25 g, 60.9 mmoles) was dissolved in anhydrous acetone (200 ml). The solution was chilled in an ice bath and hydrogen chloride was bubbled in for 15–20 mins. After half an hour, the reaction mixture was diluted with water (200 ml). A crystalline solid separated which was filtered, washed with water and dried to obtain 26.5 g of the product and 4.0 g from mother liquor.

Yield: –97.5% m.p. 207°–209° C.

EXAMPLE 2

6β,7β-Dihydroxy-8,13-epoxy-1,9-O-isopropylidene-labd-14-en-11-one (IV)

7β, Acetoxy-6β-hydroxy-1,9-O-isopropylidene-8,13-epoxy-labd-14-en-11-one (34.4 g, 76.4 mmoles) was dissolved in methanol (600 ml). To this solution was added an aqueous solution of sodium hydroxide (10%, 130 ml). It was stirred at 50° C. for 0.5 hour. The mixture was cooled and diluted with—400 ml ice-cold water. The product which separated was filtered, washed till free of alkali and dried to afford 30.2 g cf the desired product. Additional 0.7 g obtained from mother liquor.

Yield: 99% m.p. 116°–117° C.

The two reactions above were carried out sequentially on 100 g forskolin to give 104.5 g of the product.

Yield: –97%, m.p. 116°–117° C.

EXAMPLE 3

7β-Acryloyloxy-6β-hydroxy-1,9-O-isopropylidene-8,13-epoxy-labd-14-en-11-one (V)

6β, 7β-Dihydroxy-8,13-epoxy-1,9-O-isopropylidene-labd-14-en-11-one (10 g, 24.51 mmoles) was dissolved in toluene (200 ml) and triethylamine (20 ml); 43.5 mmole). To this mixture was added dropwise, a solution of β- chloropropionyl chloride (4.5 ml, 56.5 mmole) in toluene (20 ml) under ice-cold (0°–5° C.) conditions. After the addition was complete, the reaction mixture was allowed to stir at room temperature (25°–30° C.) for a period of three hours.

After the completion of the reaction, the reaction mixture was poured into ice-water (250 ml). The organic layer was separated. The aqueous layer was extracted using ethyl acetate. The combined organic layers were washed successively with water. 2N hydrochloric acid and brine. It was dried over anhydrous sodium sulfate, filtered through a short path silica gel bed, and evaporated to dryness in vacuo. The residue was crystallised from ethyl acetate:petroleum ether (60°–80° C.).

Yield: 9.33 g (90%), m.p. 180°–182° C.

EXAMPLE 4

6β-Acryloyloxy-7β-hydroxy-1,9-O-isopropylidene-8,13-epoxy-labd-14-en-11-one (VI)

7β-Acryloyloxy-6β-hydroxy-1,9-O-isopropylidene-8,13-epoxy-labd-14-en-11-one (1.0 g, 2.16 mmole) was dissolved in acetonitrile (20 ml). This solution was cooled to 0.5° C. and to it was added dropwise with stirring an aqueous solution of sodium hydroxide (0.4N, 10 ml). The reaction mixture was stirred for 3.5 hours. During this period the product separated out. It was filtered, washed with water and dried to yield 900 mg of the desired compound. Crystallised from acetone:petroleum ether (60°–80° C.).

Yield: 90%, m.p. 235°–236° C.

EXAMPLE 5

7β-Acetoxy-6β-acryloyloxy-1,9-O-isopropylidene-8,13-epoxy-labd-14-en-11-one (VII)

6β-Acryloyloxy-7β-hydroxy-1,9-O-isopropylidene-8,13-epoxy-labd-14-en-11-one (3.15 g, 6.81 mmoles) was dissolved in a mixture of pyridine (10 ml) and acetic anhydride (5 ml). The resulting mixture was left overnight at room temperature. It was poured into ice-water and the solid was collected by filtration. It was crystallised from a mixture of methylene chloride:petroleum ether (60–80).

Yield: 3.19 g, 93%, m.p. 155°–158° C.

Similarly 6β-[3-(dimethylaminopropionyl)oxy]-7β-hydroxy-1,9-O-isopropylidene-8,13-epoxy-labd-14-en-11-one was acetylated to obtain 7β-Acetoxy-6β-[3-(dimethylaminopropionyl)oxy]-1,9-O-isopropy-lidene-8,13-opoxy-labd-14-en-11-one as an oil (VIII).

EXAMPLE 6

7β-Acetoxy-6β-[3-(dimethylaminopropionyl)oxy]-1,9-dihydroxy-8,13-epoxy-labd-14-en-11-one hydrochloride (I,$NR_1R_2$=$N(CH_3)_2$;

7β-Acetoxy-6β-acryloyloxy-1,9-O-isopropylidene,8,13-epoxy-labd-14-en-11-one (5.04 g, 10 mmole) was dissolved in toluene (50 ml). The solution was chilled to 0°–5° C. and to it was added an excess (40 ml) of a 10% solution of N,N-dimethylamine in toluene. On allowing it to stand overnight, the reaction had gone to completion. The solvent was evaporated under reduced pressure to obtain 7β-Acetoxy-6β-[3-(dimethylaminopionyl)oxy]-1,9-O-isopropylidene-8,13-epoxy-labd-14-ene-11-one as an oil (VIII). It was dissolved in anhydrous ethyl ether and treated with an ethereal HCl solution to convert it into hydrochloride salt.

A solution of 7β-acetoxy-6β[3-(dimethylaminopropyl)oxy]-8,13-epoxy-1,9-O-isopropyliden-labd-14-en-11-one hydrochloride (586 mg) in water (20 ml) and approximately 5 ml of 3N HCl to maintain pH at ca. 1.0 was stirred at 30°–40° C. for 3.5 hours. The mixture was then diluted with ice water, basified with 5% aqueous $NaHCO_3$ and extracted with ethyl acetate. The organic layer was washed with water, dried (anhydrous $Na_2SO_4$), filtered and the filtrate concentrated to obtain a residue. It was converted to the hydrochloride using ethereal HCl, 484 mg, mp. 265°–167° C. (methanol-ether), yield 88%.

Similarly the following compounds were prepared.

7β-Acetoxy-6β-[3-(piperidinopropionyl)oxy]-8,13-epoxy-1α,9α-O-isopropylidene-labd-14-en-11-one was prepared and converted to 7β-Acetoxy-6β-[3-(piperidinopropionyl)oxy]-1α,9α-dihydroxy-8,13-epoxy-labd-14-11-one hydrochloride hemihydrate, m.p. 237°–239° C.

7β-Acetoxy-6β-[(3-N-methylpiperazinopropionyl)oxy]-8,13- epoxy-1,9-O-isopropylidene-labd-14-en-11-one was prepared and converted to 7β-Acetoxy-6β-[(3-N-methylpiperazinopropionyl)oxy]-1,9-dihydroxy-8,13-epoxy-labd-14-en-11-one.

7β-Acetoxy-6β[(3-morpholinopropionyl)oxy]-8,13-epoxy-1,9-O-ispopropylidene-labd-14-en-11-one was prepared and converted to 7β-Acetoxy-6β-[(3-morpholinopropionyl)oxy]-1,9-dihydroxy-8,13-epoxy-labd-14-en-11-one hydrochloride, m.p. 198°–200° C.

EXAMPLE 7

7β-Hydroxy-6β-(3-(dimethylaminopropionyl)oxy)-8,13-epoxy-1,9-O-isopropylidene-labd-14-en-11-one (Compound IX)

It was prepared in a manner analogue to that described in Example 6, para 1, starting from 7β-hydroxy-6β-acryloyloxy-1,9-O-isopropylidene-8,13-epoxy-labd-14-en-11-one.

EXAMPLE 8

6β,7β-Dihydroxy-8,13-epoxy-1,9-O-isopropylidene-labd-14-en-11-one (Compound IV)

Using Forskolin (100 g), the procedure as in Example 1 was adapted. After formation of the desired compound III, instead of dilution with water, the pH of the reaction mixture was adjusted to 7.0 with the addition of 10% aqueous sodium hydroxide. Acetone was removed under reduced pressure. The residue suspension was then treated essentially as described in Example 2 to give the desired compound (104.5) Yield—97%.

EXAMPLE 9

7β-Acetoxy-6β-[3-(dimethylaminopropionyl)oxy]-1,9-O-isopropyl-idene-8,13-epoxy-labd-14-en-11-one (Compound VIII)

6β-Acrylyloxy-7β-hydroxy-1,9-O-isopropylidene-8,13-epoxy-labd-14-en-11-one (1.37 g, 2.96 mmole) was dissolved in a mixture of pyridine (3.5 ml) and acetic anhydride (0.9 ml). The resulting clear solution was left overnight at room temperature. To this mixture was added aqueous dimethylamine solution (5 ml, 40%). After stirring for 1 hour, the reaction mixture was poured into ice-water. A solid separated out and was collected by filtration. It was washed with water and dried to obtain 1.56 g of product. Yield 96%.

EXAMPLE 10

6β-Acryloyloxy-7β-hydroxy-1,9-O-isopropylidene-8,13-epoxy-labd-14-en-11-one

7β-Acryloyloxy-6β-hydroxy-1,9-O-isopropylidene-8,13-epoxy-labd-14-en-11-one (1.16 g, 2.51 mmole) was dissolved in isopropanol (23 ml). The solution was cooled to 0° C., and to it was added a 2.5% solution of aqueous sodium hydroxide (0.29 g dissolved in 11.6 ml water). The reaction mixture was stirred at 0° C. for 1.5 hours and then diluted with water. The product which separated out was filtered, washed with water and dried to yield 1.12 g.

Yield: 96.5%, m.p. 234°–235° C.

Similar results were obtained in the above process by substituting isopropanol with acetone.

EXAMPLE 11

7β-Acetoxy-6β-[3-(N-dimethylaminopropionyl)oxy]-8,13-epoxy-labd-14-en-11-one hydrochloride A suspension of 7β-acetoxy-6β-[3-(N-dimethylaminopropionyl)oxy]-8,13-epoxy-1,9-O-isopropylidene-labd-14-en-11-one (2.20 g, 4.0 mmole) was stirred with 2N hydrochloric acid (40 ml) at room temperature. After half an hour a clear solution was obtained which on further stirring for 2.5 hours and chilling to 0° C. provided the desired product in a crystalline form. It was filtered and dried to yield 1.98 g. Yield: 91%, m.p. 265°–267° C.

Tabele I

PMR DATA FOR THE WORKING EXAMPLES

Working Examples

Example 1 (Compound III)

PMR ($CDCl_3$): δ=5.86 (d of d, $J_{trans}$=17 Hz, $J_{cis}$=10.8 Hz, vinylic-H), 5.24 (d, $J_{6,7}$=4 Hz, 7-CH), 5.18 (d of d, $J_{trans}$=17 Hz, $J_{gem}$=2 Hz, vinylic-H), 5.49 (d of d, $J_{cis}$=10.8 Hz, $J_{gem}$=2 Hz, vinylic-H), 4.4 (brt, 4-CH), 4.26 (brt, 1β-CH), 2.98, (d, $J_{gem}$=18 Hz, 12-CH), 2.6 (d, $J_{gem}$=18 Hz, 12-CH), 2.2 (d, $J_{5,6}$=2 Hz, 5-CH), 2.14 (s, $COCH_3$), 1.6, 1.52, 1.4, 1.04 (s, 5×$CH_3$), 1.32 (s,

Example 2 (Compound IV)

PMR (CDCl$_3$):δ=6.0 (d of d, J$_{cis}$=10.8 Hz, J$_{trans}$=17 Hz, vinylic-H), 5.1 (d of d, J$_{trans}$=17 Hz, J$_{gem}$=2 Hz, vinylic-H), 4.94 (d of d, J$_{cis}$=10.8 Hz, J$_{gem}$=2 Hz, vinylic-H), 4.44 (bs, 6-CH), 4.26 (bs, 2β-CH), 3.96 (d, J$_{6,7}$=4 Hz, 7-CH), 2.98 (d, J$_{gem}$=18 Hz, 12-CH), 2.62 (d, J$_{gem}$=18 Hz, 12-CH), 2.1 (d, J$_{5,6}$=3 Hz, 5-CH), 1.6, 1.42, 1.4, 1.08 (s, 5×CH$_3$), 1.3 (s,

Example 3 (Compound V)

PMR (CDCl$_3$): δ=6.5–5.7 (s, vinylic-4Hs), 5.32 (d, J$_{6,7}$=4 Hz, 7-CH), 5.16 (d of d, J$_{trans}$=2 Hz, vinylic-H), 4.36 (d of d, J$_{cis}$=10.8 hz, J$_{gem}$=2 Hz, vinylic-H), 4.4 (bs, 6-CH), 4.24 (bs, 1β-CH), 2.56 (d, J$_{gem}$=18 Hz, 12-CH), 2.58 (d, J$_{gem}$=18 Hz, 12-CH), 2.22 (d, J$_{5,6}$=3 Hz, 5-CH), 1.68, 1.64, 1.48, 1.2, 1.0 (s, 5×CH$_3$), 1.36 (s,

Example 4 (Compound VI)

PMR (CDCl$_3$):δ=6.4–5.7 (m, vinylic-4Hs), 5.1 (d of d, J$_{trans}$=17 Hz, J$_{gem}$=2 Hz, vinylic-H), 4.92 (d of d, J$_{cis}$=10.8 Hz, J$_{gem}$=2 Hz, vinylic-H), 4.28 (bs, 6-CH), 4.16 (d, J$_{6,7}$=4 Hz, 7-CH), 3.0 (d, J$_{gem}$=18 Hz, 12-CH), 2.36 (d, J$_{gem}$=18 Hz, 12-CH), 2.36 (d, J$_{5,6}$=3 Hz, 5-CH), 1.6, 1.42, 1.32, 1.08 (s, 5×CH$_3$), 1.32 (s,

Example 5 (Compound VII)

PMR (CDCl$_3$):δ=6.3–5.7 (m, vinylic-4Hs), 5.32 (d, J$_{6,7}$=4 Hz, 7-CH), 5.14 (d of d, J$_{trans}$=17 Hs, J$_{gem}$=2 Hz, vinylic-H), 4.90 (d of d, J$_{cis}$=10.8 Hz, J$_{gem}$=2 Hz, vinylic-H), 4.28 (bs, 1β-CH), 3.02 (d, J$_{gem}$=18 Hz, 12-CH), 2.62 (d, J$_{gem}$=18 Hz, 12-CH), 2.0 (s, OCOCH$_3$), 1.56, 1.52, 1.44, 1.04, 1.0 (s, 5×CH$_3$), 1.32 (s,

Example 5/6 (Compound VIII)

PMR (CDCl$_3$):δ=5.92 (d of d, J$_{cis}$=10.8 Hz, J$_{trans}$=17 Hz, vinylic-H), 5.8 (bs, 4-CH), 5.30 (d, J$_{6,7}$=4 Hz, 7-CH), 5.16 (d of d, J$_{trans}$=17 Hz, J$_{gem}$=2 Hz, vinylic-H), 4.98 (d of d, J$_{cis}$=10.8 Hz, J$_{gem}$=2 Hz, vinylic-H), 4.26 (bs, 1β-CH), 3.0 (d, J$_{gem}$=18 Hz, 12-CH), 2.62 (d, J$_{gem}$=18 Hz, 12-CH), 2.7–2.5 (m, CH$_2$—CH$_2$), 2.4 (d, J$_{5,6}$=3 Hz, 5-CH), 2.24 (s, N(CH$_3$)$_2$, 1.56, 1.50, 1.44, 1.3, 1.0 (s, 5×CH$_3$), 2.0 (s, OCOCH$_3$), 1.3 (s,

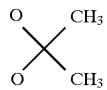

Example 6 (Compound I, NR$_1$R$_2$=N(CH$_3$)$_2$)

PMR (CDCl$_3$):δ5.96 (d of d, J$_{trans}$=17 Hz, J$_{cis}$=10.8 Hz, vinylic-H), 5.80 (bt, 6-CH), 5.48 (d, J$_{6,7}$=4 Hz, 7-CH), 5.06 (d of d, J$_{trans}$=17 Hz, J$_{gem}$=2 Hz, vinylic-H), 4.84 (d of d, J$_{cis}$=10.8 Hz, J$_{gem}$=2 Hz, vinylic-H), 4.42 (bs, 1β-CH), 3.22 (d, J$_{gem}$=18 Hz, 12-CH), 2.30 (d, J$_{gem}$=18 Hz, 12-CH), 2.84 (s, N(CH$_3$)$_2$), 2.52–3.02 (m, N-CH$_2$), 1.96 (s, OCOCH$_3$), 1.60, 1.40, 1.32, 1.02, 0.96 (s, 5×CH$_3$).

Example 7 (Compound IX, NR$_1$R$_2$=N(CH$_3$)$_2$)

PMR (CDCl$_3$):δ=6.02 (d of d, J$_{trans}$=17 Hz, J$_{cis}$=10.8 Hz, vinylic-H), 5.84 (bt, 6-CH), 5.12 (d of d, J$_{trans}$=17 Hz, J$_{gem}$=2 Hz, vinylic-H), 4.90 (d of d, J$_{cis}$=10.8 Hz, J$_{gem}$=2 Hz, vinylic-H), 4.28 (bs, 1β-CH), 4.08 (d, J$_{6,7}$=4 Hz, 7-CH), 3.0 (d, J$_{gem}$=18 Hz, 12-CH), 2.62 (d, J$_{gem}$=18 Hz, 12-CH), 2.7–2.5 (m, CH$_2$—CH$_2$), 2.24 (s, N(CH$_3$)$_2$), 1.56, 1.5, 1.3, 1.0 (s, 5×CH$_3$), 1.44 (s,

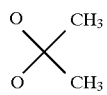

What is claimed is:

1. Process for the manufacture of 6β-(3-substitutedamino) propionyloxyforskolin derivatives of the general formula I

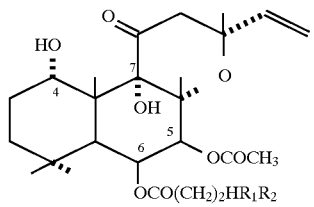

wherein R$_1$ and R$_2$ each stands for hydrogen, alkyl, aryl, aralkyl or dialkylaminoalkyl; or R$_1$ and R$_2$ together with the nitrogen to which they are attached form a heterocycle which may contain an additional heteroatom and may optionally be substituted at one or more positions by alkyl, alkoxy, hydroxyl, halogen or aryl and pharmaceutically acceptable salts thereof, which comprises:

(a) reacting forskolin (compound of formula I with OH in 6-position) with acetone in the presence of hydrogen chloride to provide the 1,9-isopropylidene derivative, (b) treating this derivative in an alkanol with alkali to obtain the 7-deacetyl derivative, (c) treating this derivative with β-halopropionylhalide in the presence of an organic base to form the 1,9-O-isopropylidene derivative of 7β-acryloyloxy-7-deacetyl forskolin, (d) treating this derivative with alkali to lead to the 1,9-O-isopropylidene derivatives of 6β-acryloyloxy-7-deacetyl forskolin, (e) which is transformed to the 7β-acetoxy derivative, (f) which is reacted with an amine of the formula

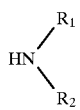

, wherein $R_1$ and $R_2$ have the definitions mentioned above, to form the (3-substituted amino) propionyloxy derivative in 6-position and (g) deprotecting the obtained compound at the 1,9-positions to obtain a compound of the formula I and (h) optionally, converting it to a pharmaceutically acceptable salt, wherein the sequence of steps (e) and (f) and also of steps (f) and (g) can be exchanged.

2. Process as claimed in claim 1, wherein in step (c) the β-halopropionylhalide is β-chloropropionyl chloride.

3. Process as claimed in claim 1 or 2, wherein in step (f) the amine is dimethylamine.

4. Process as claimed in one of claims 1 to 3, wherein steps (a) and (b) are carried out in a one-pot reaction and steps (e) and (f) are carried out in a one-pot reaction.

\* \* \* \* \*